(12) United States Patent
Yang et al.

(10) Patent No.: US 11,104,928 B2
(45) Date of Patent: *Aug. 31, 2021

(54) FERMENTATION PROCESS WITH PICHIA YEAST EXPRESSING RECOMBINANT PROTEIN

(71) Applicant: JIANGSU JLAND BIOTECH CO., LTD., Jingjiang (CN)

(72) Inventors: Shulin Yang, Nanjing (CN); Jianfeng Zhao, Jingjiang (CN); Jianmin Huang, Jingjiang (CN); Lihu Gao, Jingjiang (CN); Erfeng Du, Jingjiang (CN); Hai Tao, Jingjiang (CN); Liping Feng, Jingjiang (CN); Le Ji, Jingjiang (CN); Aimei Zhou, Jingjiang (CN)

(73) Assignee: JIANGSU JLAND BIOTECH CO., LTD., Jingjiang (CN)

( * ) Notice: Subject to any disclaimer, the term of this patent is extended or adjusted under 35 U.S.C. 154(b) by 264 days.

This patent is subject to a terminal disclaimer.

(21) Appl. No.: 16/318,549

(22) PCT Filed: Oct. 18, 2016

(86) PCT No.: PCT/CN2016/102430
§ 371 (c)(1),
(2) Date: Jan. 17, 2019

(87) PCT Pub. No.: WO2018/014452
PCT Pub. Date: Jan. 25, 2018

(65) Prior Publication Data
US 2019/0309339 A1    Oct. 10, 2019

(30) Foreign Application Priority Data
Jul. 22, 2016 (CN) .......................... 201610587122.4

(51) Int. Cl.
| C08L 89/00 | (2006.01) |
| C12P 21/00 | (2006.01) |
| C12N 1/00 | (2006.01) |
| C12P 21/02 | (2006.01) |
| C07K 14/78 | (2006.01) |
| C12N 1/16 | (2006.01) |
| C12R 1/84 | (2006.01) |

(52) U.S. Cl.
CPC .............. *C12P 21/02* (2013.01); *C07K 14/78* (2013.01); *C12N 1/16* (2013.01); *C12N 1/165* (2021.05); *C12R 2001/84* (2021.05)

(58) Field of Classification Search
CPC ............ C12N 15/8509; C12N 2533/50; C12N 15/81; C12N 15/815; C12N 15/70; C12N 1/16; C12P 21/02; C12P 21/005; C12Y 114/11004
USPC ...... 435/252.23, 455, 97, 483; 530/356, 395
See application file for complete search history.

(56) References Cited

FOREIGN PATENT DOCUMENTS

| CN | 101570771 A | 11/2009 |
| CN | 102146426 A | 8/2011 |
| CN | 102443057 A | 5/2012 |
| CN | 105779317 A | 7/2016 |
| EP | 2 502 991 A1 | 9/2012 |
| WO | WO 90/00191 A1 | 1/1990 |
| WO | WO 90/02810 A1 | 3/1990 |
| WO | WO 90/03431 A1 | 4/1990 |
| WO | WO 2014/145650 A1 | 9/2014 |

OTHER PUBLICATIONS

European Communication pursuant to Rules 70(2) and 70a(2) EPC dated Jun. 5, 2019 for Application No. 16909379.6.
Extended European Search Report dated May 17, 2019 for Application No. 16909379.6.
Lin et al., "High Density Fermentation Control of Pichia pastoris", China Biotechnology, vol. 29, No. 5 2009, pp. 120-125, along with an English abstract.
Nokelainen et al., "High-level production of human type I collagen in the yeast *Pichia pastoris*", Yeast, vol. 18, 2001, pp. 797-806.
Bahrami et al., "Two-stage Glycerol Feeding for Enhancement of Recombinant hG-CSF Production in a Fed-batch Culture of Pichia Pastoris", Biotechnology Letters, vol. 30, No. 6, Jun. 30, 2008, pp. 1081-1085.
Hu et al., "Optimization of S-adenosyl-L-methionine production in recombinant Pichia pastoris methanol-glycerol feeding strategy", Industrial Microbiology, vol. 42, No. 6, Dec. 22, 2012, pp. 63-67 (Total No. pp. 6).

(Continued)

*Primary Examiner* — Tekchand Saidha
*Assistant Examiner* — Mohammad Y Meah
(74) *Attorney, Agent, or Firm* — Birch, Stewart, Kolasch & Birch, LLP

(57) ABSTRACT

The present invention discloses a fermentation process with a *Pichia* yeast expressing a recombinant protein, in which *Pichia pastoris* is used as a fungal strain. The process comprises performing primary seed culturing to reach a fungal concentration of 20±2 g/L; then performing secondary seed culturing to reach a fungal concentration of 120±10 g/L; next proceeding to a glycerol culturing stage, wherein the amount of glycerol added in the glycerol culturing stage is 60-70 g/L; and then proceeding to a methanol-induced stage for 120±8 h after the dissolved oxygen quickly reaches a relatively stable state, to complete the fermentation process. In the present invention, a glycerol fed-batch addition stage in existing processes is omitted, and the process proceeds to a next stage as soon as glycerol is completely consumed, with no need to prepare sterilized glycerol for fluidic addition. As such, the glycerin sterilizer is omitted, the consumption of energy and resource and the waste of glycerin are reduced. Moreover, the fungal concentration has no need to be monitored, thus reducing the probability of errors, and lowering the fermentation failure caused by technical errors. Therefore, the present process is more suitable for large-scale industrial production, and brings convenience and great economic value for the industrial production of the recombinant protein.

13 Claims, 1 Drawing Sheet

(56) References Cited

OTHER PUBLICATIONS

International Search Report issued in PCT/CN2016/102430 (PCT/ISA/210), dated Apr. 25, 2017.
Gao et al., "Construction ofHuman-like Collagen Expression Vector and Its Expression in Pichia Pastoris," Journal of Nanjing University of Science and Technology (Natureal Science), vol. 32, No. 2, Apr. 2008, pp. 252-256, with English abstract.
Zhang et al., "Pichia pastoris fermentation with mixed-feeds of glycerol and methanol: growth kinetics and production improvement," J Ind Microbiol Biotechnical, vol. 30, 2003 (published online Apr. 2, 2003), pp. 210-215.

FERMENTATION PROCESS WITH PICHIA YEAST EXPRESSING RECOMBINANT PROTEIN

TECHNICAL FIELD

The present invention relates to the technical field of fermentation engineering, and particularly to a fermentation process with a *Pichia* yeast expressing a recombinant protein.

RELATED ART

*Pichia pastoris* expression system is a new type of exogenous protein expression system developed in the early 1980s. It has the advantages of simple operation, easy cultivation, fast growth, high expression level, low cost, and others of prokaryotic expression systems, and is also characterized by having modifications for exogenous proteins such as glycosylation and protein phosphorylation that are absent in prokaryotic expression systems. *Pichia pastoris* expression system is advantageous in that (1) the alcohol oxidase aox1 gene promoter is present therein, which is one of the most potent promoters having the most stringent regulatory mechanism; (2) the expression efficiency is high, and the exogenous protein expressed therein accounts for more than 90% of the total expressed proteins, which is beneficial to the separation and purification of the target protein; (3) high-density culture can be achieved in a simple synthetic medium; (4) the expression plasmid can be stably integrated at a specific site of the genome in the form of a single copy or multiple copies; and (5) the yeast can use methanol as the sole carbon source, and the medium does not require the addition of other organic matters, so as to reduce the pollution.

At present, the most commonly used expression vector and fermentation process are constructed and developed by Invitrogen, USA, with which hundreds of foreign proteins have been successfully expressed. The industrialized *Pichia pastoris* fermentation process developed by Invitrogen can be divided into primary and secondary seed culturing, a glycerol culturing stage, a glycerol fed-batch addition stage and a methanol-induced stage. The process is a commonly used fermentation process for the production of exogenous proteins by *Pichia pastoris* (Chinese Patent Nos. 201010602114.5 and 201110327865.5). The glycerol culturing stage and the glycerol fed-batch addition stage allow the fungal cells to grow and proliferate rapidly to reach an optimal fungal concentration range of high-density fermentation. These stages are very important in industrial production, and need to be monitored in real time, and the operation is complicated and difficult to control. A fungal concentration above or below this range will result in increased cost and reduced protein yield.

In the practical industrial production with a *Pichia* yeast expressing a recombinant protein, the operators are mainly ordinary workers, the complicated operation is likely to lead to a high error rate and the occurrence of technical error events, causing the final failure of the fermentation process. Therefore, simplifying the fermentation process with a *Pichia* yeast expressing a recombinant protein, especially simplifying the complicated processes in the glycerol culturing and glycerol fed-batch addition stages in the existing fermentation process, can not only reduce the production cost, but also reduce the probability of error and lower the fermentation failure caused by technical errors, thus bringing convenience and great economic value for the industrial production of the recombinant protein.

SUMMARY

To simplify the existing fermentation process with a *Pichia* yeast expressing a recombinant protein, an object of the present invention is to provide a fermentation process with a *Pichia* yeast expressing a recombinant protein that has simple process, convenient and feasible operations, high yield and high purity of recombinant protein, and is applicable to large-scale industrial production.

The following technical solution is adopted in the present invention.

A fermentation process with a *Pichia* yeast expressing a recombinant protein is provided, in which *Pichia pastoris* is used as a fungal strain. The process comprises performing primary seed culturing to reach a fungal concentration of 20±2 g/L; then performing secondary seed culturing to reach a fungal concentration of 120±10 g/L; next proceeding to a glycerol culturing stage, where the amount of glycerol added in the glycerol culturing stage is 60-70 g/L; and then proceeding to a methanol-induced stage for 120±8 h after the dissolved oxygen quickly reaches a relatively stable state, to complete the fermentation process.

The *Pichia pastoris* was deposited in China General Microbiological Culture Collection Center (CGMCC) under CGMCC Accession No. 5021 on Jun. 29, 2011, and fully disclosed in Chinese Patent No. 201110327865.5.

The primary seed culturing mentioned in the present invention is carried out through an existing conventional process comprising specifically inoculating the fungal strain *Pichia pastoris* to a seed medium, and incubating in a shake flask at 30° C. for 24 to 36 hrs, until the wet weight of the fungal cells reaches 20±2 g/L.

The secondary seed culturing mentioned in the present invention is carried out through an existing conventional process comprising specifically inoculating the primary seed culture completely in a fermentation medium, and incubating at 30° C. until the wet weight of the fungal cells reaches 120±10 g/L, during which the pH is adjusted with aqueous ammonia and controlled to 5.0, and the dissolved oxygen is controlled to 20-30%.

The glycerol culturing stage mentioned in the present invention comprises specifically inoculating the secondary seed culture in a fermentation medium, adding glycerol in an amount of 60-70 g/L, and culturing at 30° C., during which the pH is adjusted with aqueous ammonia and controlled to 5.0, the aeration rate is 30 m³/h, the stirring speed is 300-500 rpm, and when the dissolved oxygen rises sharply, the fungi cells are starved for 1 h to deplete the glycerol.

The methanol-induced stage mentioned in the present invention is performed through an existing conventional process and comprises specifically a controlled temperature of 30° C. and pH of 5.0 in the induction stage, the methanol feed is set to link with the dissolved oxygen, when the dissolved oxygen is higher than 20%, methanol is added in a fed-batch mode, and when the dissolved oxygen is less than 20%, the methanol fed-batch addition is stopped; the fermentation is completed after 120±8 h of induction; and the fermentation liquid is centrifuged, and the supernatant after centrifugation is collected, concentrated, ultrafiltered, nanofiltered, decolorized, and desalted to obtain a recombinant human collagen.

Compared with the prior art, the present invention has the following advantages:

(1) The fermentation process with a *Pichia* yeast of the present invention requires no preparation of sterilized glycerol for fluidic addition. As such, the glycerol sterilizer is omitted, the consumption of energy and resource and the waste of glycerol are reduced.

(2) after the glycerol is depleted, the process proceed to a next step, which effectively solves the problems that the fermentation process with a *Pichia* yeast is complicated and the protein yield is unstable, and shortens the time of the glycerol culturing stage.

(3) The fermentation process with a *Pichia* yeast of the present invention is simple and easy, the fungal concentration has no need to be monitored, the probability of error is reduced, and the process is convenient for implementation by the production staff and is more suitable for large-scale industrial production.

Compared with previous processes, the process of the present invention is simple, the yield of the target protein is comparable, the recovery rate is increased to about 70%, and the purity is 95% or high. Thus, the present process is more suitable for large-scale industrial production of recombinant human collagen.

DETAILED DESCRIPTION

Figure 1:
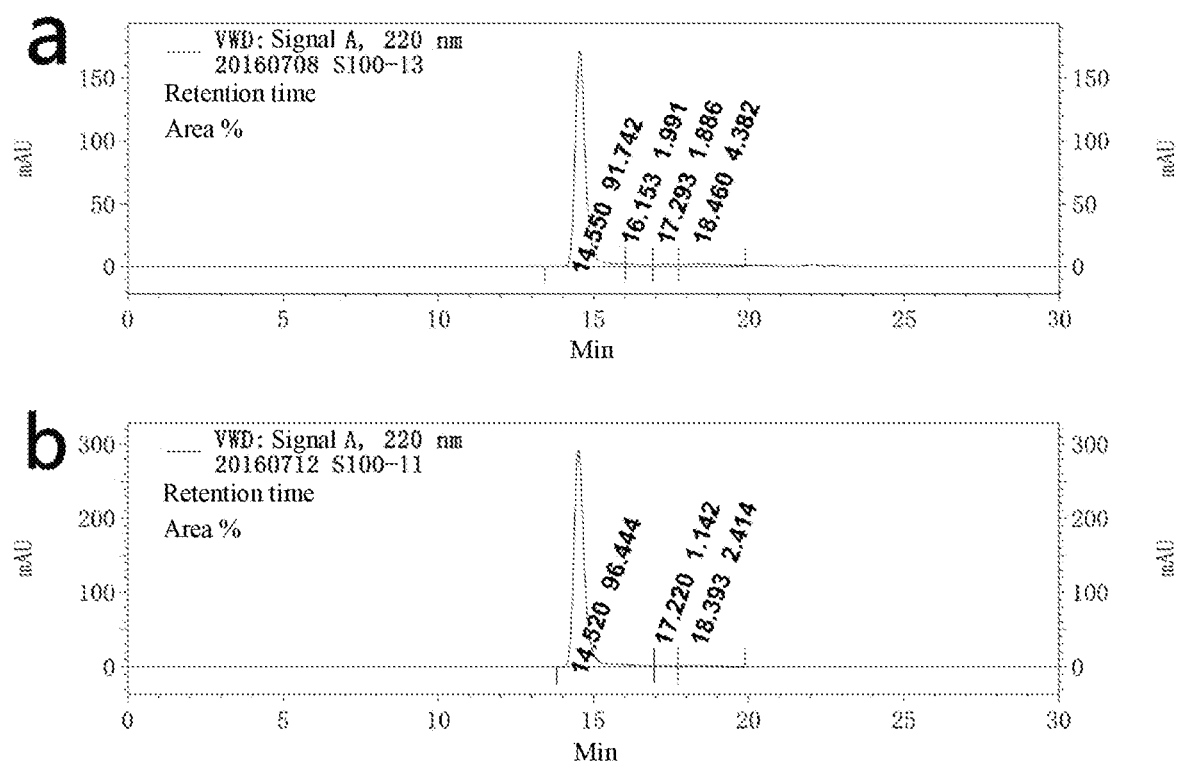
FIG. 1 shows HPLC chromatograms of the fermentation liquids obtained in Comparative Example 1 (a) and Example 2 (b) after separation and purification.

The fermentation process with a *Pichia* yeast expressing a recombinant protein of the present invention includes primary seed culturing, secondary seed culturing, a glycerol culturing stage, and a methanol fed-batch addition stage.

The existing fermentation process with a *Pichia* yeast expressing a recombinant protein includes primary seed culturing, secondary seed culturing, a glycerol culturing stage, a glycerol fed-batch addition stage, and a methanol fed-batch addition stage.

Unless otherwise stated, the fungal strain and media used in the examples and comparative examples of the present invention are basically as follows:

1. Fungal strain: *Pichia pastoris*, deposited in China General Microbiological Culture Collection Center (CGMCC) under CGMCC Accession No. 5021 on Jun. 29, 2011, and fully disclosed in Chinese Patent No. 201110327865.5.

2. Media:

(1) The medium for primary seed culturing is BMGY medium having a composition of:

| yeast extract powder | 10 g/L | tryptone | 20 g/L |
|---|---|---|---|
| potassium phosphate buffer pH 6.0 | 100 mmol/L | yeast basic nitrogen source | 13.4 g/L |
| biotin | 0.2 mg/L | Glycerol | 10 g/L |

(2) The medium for secondary seed culturing has a composition of:

| Glycerol | 40 g/L | $K_2SO_4$ | 18.2 g/L |
|---|---|---|---|
| $H_3PO_4$ | 26.7 mL/L | $CaSO_4 \cdot 2H_2O$ | 0.93 g/L |
| $MgSO_4$ | 14.9 g/L | KOH | 4.13 g/L |
| PTM1 | 4.35 mL/L | | |

(3) The fermentation medium has a composition of

| $K_2SO_4$ | 18.2 g/L | $H_3PO_4$ | 26.7 mL/L |
|---|---|---|---|
| $CaSO_4 \cdot 2H_2O$ | 0.93 g/L | $MgSO_4$ | 14.9 g/L |
| KOH | 4.13 g/L | PTM1 | 4.35 mL/L |

The concentration of glycerol in the comparative example is 40 g/L, and a 50% aqueous solution of glycerol is added in a fed-batch mode. The concentration of glycerol in the examples is 55-75 g/L. After the completion of the glycerol culturing stage, the process proceeds to the methanol fed-batch addition stage and the medium is not changed. PTM1 has a composition of

| $CuSO_4 \cdot 5H_2O$ | 6.0 g/L | NaI | 0.08 g/L |
|---|---|---|---|
| $MnSO_4 \cdot H_2O$ | 3.0 g/L | $Na_2MoO4 \cdot 2H_2O$ | 0.2 g/L |
| $H_3BO_3$ | 0.02 g/L | $CoCl_2 \cdot 6H_2O$ | 0.5 g/L |
| $ZnCl_2$ | 20.0 g/L | $FeSO_4 \cdot 7H_2O$ | 65.0 g/L |
| biotin | 0.2 g/L | concentrated $H_2SO_4$ | 5.0 mL/L |

Example 1

A fermentation process with a *Pichia* yeast expressing a recombinant protein comprises the following steps.

(1) Primary Seed Culturing

A glycerol-preserved fungal strain was inoculated into a shake flask containing 200 mL of a seed medium, incubated at 30° C. and 250 rpm for 24 to 36 hrs, until the wet weight of the fungal cells reached 20±2 g/L.

(2) Secondary Seed Culturing

The primary seed culture was completely inoculated in a 100 L fermentor containing 60 L of a fermentation medium, and incubated at 30° C. until the wet weight of the fungal cells reached 120±10 g/L, during which the pH was adjusted with aqueous ammonia and controlled to 5.0, and the dissolved oxygen was controlled to 20-30%.

(3) Incubation and Induction to Express in Fermentor

The secondary seed culture was inoculated in a 1000 L fermentor containing 60 L of a fermentation medium, glycerol was added in an amount of 60 g/L, and cultured at 30° C., during which the pH was adjusted with aqueous ammonia and controlled to 5.0, the aeration rate was 30 m³/h, the stirring speed was 300-500 rpm, and when the dissolved oxygen rose sharply, the fungi cells were starved for 1 h to deplete the glycerol.

Then the methanol-induced stage began. In the induction stage, the temperature was controlled to 30° C., and the pH was controlled to 5.0. The methanol feed was set to link with the dissolved oxygen. When the dissolved oxygen was higher than 20%, methanol was added in a fed-batch mode, and when the dissolved oxygen was less than 20%, the methanol fed-batch addition was stopped. A plateau phase was reached after 112 h of induction; and the fermentation liquid was discharged after 120 h of induction. The fermentation liquid after induction to express was centrifuged, and the supernatant after centrifugation was collected, concentrated, ultrafiltered, nanofiltered, decolorized, and desalted to obtain a recombinant human collagen.

Example 2

This example differed from Example 1 in that the amount of glycerol added was 65 g/L, and the other steps were the same as in those in Example 1.

Example 3

This example differed from Example 1 in that the amount of glycerol added was 70 g/L, and the other steps were the same as in those in Example 1.

Comparative Example 1

This comparative example differed from Example 1 in that the amount of glycerol added was 55 g/L, and the other steps were the same as in those in Example 1.

Comparative Example 2

This comparative example differed from Example 1 in that the amount of glycerol added was 75 g/L, and the other steps were the same as in those in Example 1.

Comparative Example 3

(1) Primary Seed Culturing
A glycerol-preserved fungal strain was inoculated into a shake flask containing 200 mL of a seed medium, incubated at 30° C. and 250 rpm for 24 to 36 hrs, until the wet weight of the fungal cells reached 20±2 g/L.

(2) Secondary Seed Culturing
The primary seed culture was completely inoculated in a 100 L fermentor containing 60 L of a fermentation medium, and incubated at 30° C. until the wet weight of the fungal cells reached 120±10 g/L, during which the pH was adjusted with aqueous ammonia and controlled to 5.0, and the dissolved oxygen was controlled to 20-30%.

(3) Incubation and Induction to Express in Fermentor
The secondary seed culture was inoculated in a 1000 L fermentor containing 60 L of a fermentation medium, glycerol was added in an amount of 40 g/L, and cultured at 30° C., during which the pH was adjusted with aqueous ammonia and controlled to 5.0, the aeration rate was 30 m³/h, and the stirring speed was 300-500 rpm. When the dissolved oxygen rose sharply, glycerol was added in a fed-batch mode, the pH was controlled to 5.0, and the dissolved oxygen was controlled to above 20%. When the fungal concentration reached 160±10 g/L, the glycerol fed-batch addition was stopped and the fungi cells were starved for 1 h to deplete the glycerol.

Then the methanol-induced stage began. In the induction stage, the temperature was controlled to 30° C., and the pH was controlled to 5.0. The methanol feed was set to link with the dissolved oxygen. When the dissolved oxygen was higher than 20%, methanol was added in a fed-batch mode, and when the dissolved oxygen was less than 20%, the methanol fed-batch addition was stopped. A plateau phase was reached after 112 h of induction; and the fermentation liquid was discharged after 120 h of induction. The fermentation liquid after induction to express was centrifuged, and the supernatant after centrifugation was collected, concentrated, ultrafiltered, nanofiltered, decolorized, and desalted to obtain a recombinant human collagen.

FIG. 1 shows HPLC chromatograms of the fermentation liquids obtained in Comparative Example 1 and Example 2 after separation and purification, in which the peak is a recombinant human collagen, a is Comparative Example 1, and b is Example 2. It can be seen from the figure that after the fermentation liquid of Comparative Example 1 is separated and purified, the protein purity is 91.7%, and after the fermentation liquid of Example 2 is separated and purified, the protein purity is 96.4%. The purity of the recombinant human collagen obtained by the fermentation process of the present invention is better than that of the comparative example.

The fermentation effect in each of the examples and the comparative examples were tested by determining the wet weight of fungal cells before fluidic addition of methanol, the collagen yield, the protein recovery rate and the protein purity. The specific test results are shown in Table 1.

TABLE 1

Results of fermentation for each example and comparative example

| | Wet weight of fungal cells before fluidic addition of methanol | Collagen yield | Protein recovery rate | Protein purity |
|---|---|---|---|---|
| Comparative Example 1 | 147.8 g/L | 14.51 g/L | 67.2% | 91.7% |
| Comparative Example 2 | 186.2 g/L | 15.43 g/L | 67.9% | 93.4% |
| Comparative Example 3 | 166.7 g/L | 16.82 g/L | 62.8% | 92.1% |
| Example 1 | 163.3 g/L | 16.93 g/L | 70.7% | 95.3% |
| Example 2 | 169.4 g/L | 17.02 g/L | 73.3% | 96.4% |
| Example 3 | 177.8 g/L | 16.87 g/L | 72.8% | 95.9% |

It can be seen from the table that with the fermentation process of the present invention, the recovery rate of the recombinant human collagen is 70% or higher, and the purity is 95% or higher, which are superior to those of the comparative examples. The collagen concentration and purity after purification are determined by HPLC. The protein expression level is comparable to that of the comparative example, and the protein yield and purity are higher than those of the comparative examples. In summary, the process of the present invention is simple and more suitable for large-scale industrial production of recombinant human collagen.

The invention claimed is:

1. A fermentation process for producing a recombinant human collagen using a fungal strain *Pichia pastoris* comprising:
    performing primary seed culturing to reach a fungal net weight of 20±2 g/L;
    performing secondary seed culturing to reach a fungal net weight of 120±10 g/L;
    preforming a glycerol culturing stage, wherein the amount of glycerol added in the glycerol culturing phase is 60-70 g/L; and
    performing a methanol-induced stage for 120±8 h after dissolved oxygen quickly reaches a relatively stable state, to complete the fermentation and provide a recombinant human collagen.

2. The fermentation process according to claim 1, wherein the primary seed culturing comprises inoculating the fungal strain *Pichia pastoris* to a seed medium, and incubating in a shake flask at 30° C. for 24 to 36 hrs, until the wet weight of the fungal cells reaches 20±2 g/L.

3. The fermentation process according to claim 1, wherein the secondary seed culturing comprises inoculating the primary seed culture completely in a fermentation medium, and incubating at 30° C. until the wet weight of the fungal cells reaches 120±10 g/L, during which the pH is adjusted with aqueous ammonia and controlled to 5.0, and the dissolved oxygen is controlled to 20-30%.

4. The fermentation process according to claim 1, wherein the glycerol culturing stage comprises inoculating the secondary seed culture in a fermentation medium, adding glycerol in an amount of 60-70 g/L, and culturing at 30° C., during which the pH is adjusted with aqueous ammonia and controlled to 5.0, the aeration rate is 30 m$^3$/h, the stirring speed is 300-500 rpm, and when the dissolved oxygen rises sharply, the fungi cells are starved for 1 h to deplete the glycerol.

5. The fermentation process according to claim 1, wherein the methanol-induced stage comprises a controlled temperature of 30° C. and pH of 5.0; and
wherein the methanol feed is set to link with a dissolved oxygen amount, when the dissolved oxygen amount is higher than 20%, methanol is added in a fed-batch mode, and when the dissolved oxygen amount is less than 20%, the methanol fed-batch addition is stopped.

6. The fermentation process according to claim 1, wherein the methanol-induced stage comprises a controlled temperature of 30° C. and pH of 5.0.

7. The fermentation process according to claim 1, wherein in the methanol-induced stage, a methanol feed is set to link with a dissolved oxygen amount, wherein when the dissolved oxygen amount is higher than 20%, methanol is added in a fed-batch mode, and wherein when the dissolved oxygen amount is less than 20%, the methanol fed-batch addition is stopped.

8. The fermentation process according to claim 1, further comprising, after the fermentation is complete:
centrifuging a fermentation liquid, to obtain a supernatant; and
concentrating the supernatant to obtain a concentrated supernatant.

9. The fermentation process according to claim 8, further comprising, after the centrifuging:
filtering the concentrated supernatant by ultrafiltration and/or nanofiltration.

10. The fermentation process according to claim 8, further comprising, after the centrifuging:
decolorizing the concentrated supernatant.

11. The fermentation process according to claim 8, further comprising, after the centrifuging:
desalting the concentrated supernatant.

12. The fermentation process according to claim 1, further comprising:
isolating the recombinant human collagen.

13. The fermentation process according to claim 12, wherein the isolated recombinant human collagen has a recovery rate of the recombinant human collagen of 70% or higher, with a purity of 95% or higher.

* * * * *